United States Patent [19]

Dennis et al.

[11] Patent Number: 4,496,769

[45] Date of Patent: Jan. 29, 1985

[54] PROCESS FOR THE PREPARATION OF ALDEHYDES BY HYDROFORMYLATION OF OLEFINS

[75] Inventors: Alan J. Dennis, Middlesbrough; George E. Harrison, Billericay; James P. Wyber, Stockton-on-Tees, all of England

[73] Assignee: Davy McKee (London) Limited, London, England

[21] Appl. No.: 501,920

[22] Filed: Jun. 7, 1983

[30] Foreign Application Priority Data

Jun. 11, 1982 [GB] United Kingdom ............... 8217038

[51] Int. Cl.³ ............................................. C07C 45/50
[52] U.S. Cl. ............................................. 568/454
[58] Field of Search .................... 568/454, 909, 882

[56] References Cited

U.S. PATENT DOCUMENTS

| | | | |
|---|---|---|---|
| 3,499,933 | 3/1970 | Pruett et al. | 568/454 |
| 3,527,809 | 9/1970 | Pruett et al. | 568/454 |
| 3,547,964 | 12/1970 | Olivier et al. | 260/429 R |
| 3,560,539 | 2/1971 | Booth | 260/429 R |
| 3,641,076 | 2/1972 | Booth | 260/429 R |
| 3,644,446 | 2/1972 | Booth et al. | 260/429 R |
| 3,859,359 | 1/1975 | Keblys | 568/454 |
| 3,907,847 | 9/1975 | Keblys | 260/429 R |
| 3,917,661 | 11/1975 | Pruett et al. | 568/454 |
| 3,933,919 | 1/1976 | Wilkinson | 568/454 |
| 3,956,177 | 5/1976 | Zuech | 252/428 |
| 4,096,192 | 6/1978 | Bhatia et al. | 568/852 |
| 4,101,588 | 7/1978 | Nienburg et al. | 568/454 |
| 4,107,079 | 8/1978 | Chevallier et al. | 252/429 |
| 4,108,905 | 8/1978 | Wilkinson | 568/454 |
| 4,135,911 | 1/1979 | Balmat | 252/413 |
| 4,151,209 | 4/1979 | Paul et al. | 568/454 |
| 4,158,020 | 6/1979 | Stautzenberger et al. | 568/454 |
| 4,195,042 | 3/1980 | Zuech | 568/454 |
| 4,200,591 | 4/1980 | Hignett et al. | 568/454 |
| 4,200,592 | 4/1980 | Hignett et al. | 568/454 |
| 4,224,255 | 9/1980 | Smith | 568/454 |
| 4,262,142 | 4/1981 | Sherman et al. | 568/454 |
| 4,267,383 | 5/1981 | Booth | 568/454 |
| 4,302,394 | 11/1981 | Dennis et al. | 260/343.6 |
| 4,400,547 | 8/1983 | Dawes | 568/454 |
| 4,414,420 | 11/1983 | Harris | 568/454 |

FOREIGN PATENT DOCUMENTS

| | | | |
|---|---|---|---|
| 0003753 | 1/1979 | European Pat. Off. | 568/454 |
| 0028892 | 10/1980 | European Pat. Off. | 568/454 |
| 10765 | 5/1969 | Japan . | |
| 40326 | 5/1973 | Japan . | |
| WO80/00081 | 11/1980 | PCT Int'l Appl. | 568/454 |
| 988941 | 6/1961 | United Kingdom | 568/454 |
| 995459 | 8/1962 | United Kingdom | 568/454 |
| 1243189 | 12/1967 | United Kingdom | 568/454 |
| 1243190 | 12/1967 | United Kingdom | 568/454 |
| 1207561 | 1/1968 | United Kingdom | 568/454 |
| 1228201 | 4/1968 | United Kingdom | 568/454 |
| 1338225 | 12/1969 | United Kingdom | 568/454 |
| 1325199 | 8/1970 | United Kingdom | 568/454 |
| 1338237 | 12/1970 | United Kingdom . | |
| 1448090 | 11/1973 | United Kingdom | 568/454 |
| 1455645 | 4/1974 | United Kingdom | 568/454 |
| 1461900 | 7/1975 | United Kingdom | 568/454 |
| 1462342 | 7/1975 | United Kingdom | 568/852 |
| 1460870 | 7/1975 | United Kingdom | 568/454 |
| 1463947 | 10/1975 | United Kingdom | 568/454 |
| 1557396 | 3/1977 | United Kingdom | 568/852 |
| 1582010 | 4/1977 | United Kingdom . | |
| 1586805 | 9/1977 | United Kingdom | 568/454 |
| 2000124 | 5/1978 | United Kingdom | 568/454 |
| 2068377 | 2/1981 | United Kingdom | 568/454 |

OTHER PUBLICATIONS

Condensations of Carbonyl Compounds with Phosphite Esters, F. Ramirez, Pure & Applied Chemistry, (1964), vol. 9, 337-369.
Low Pressure Oxo Process Yields a Better Product Mix, Chemical Engineering, Dec. 5, 1977, pp. 110-115.

Primary Examiner—Werren B. Lone
Attorney, Agent, or Firm—Bernard, Rothwell & Brown

[57] ABSTRACT

A process for the production of an aldehyde by hydroformylation of an olefin comprises:

providing a hydroformylation zone containing a charge of a liquid reaction medium having dissolved therein a complex rhodium hydroformylation catalyst comprising rhodium in complex combination with carbon monoxide and with an organic phosphite ligand of the general formula:

$$(RO)_3P \qquad (I)$$

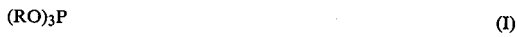

in which each R represents an optionally substituted hydrocarbyl radical;

supplying said olefin to the hydroformylation zone;

maintaining temperature and pressure conditions in the hydroformylation zone conducive to hydroformylation of the olefin;

supplying make-up hydrogen and carbon monoxide to the hydroformylation zone;

recovering from the liquid hydroformylation medium a hydroformylation product comprising at least one aldehyde; and supplying make-up phosphite ligand to the hydroformylation zone at a rate sufficient to maintain a predetermined level of free phosphite ligand in the hydroformylation medium.

10 Claims, No Drawings

PROCESS FOR THE PREPARATION OF ALDEHYDES BY HYDROFORMYLATION OF OLEFINS

This invention relates to a hydroformylation process, particularly a process for the hydroformylation of olefins to give aldehydes.

Hydroformylation is a well known reaction in which an olefin (usually a terminal olefin) is reacted under suitable temperature and pressure conditions with hydrogen and carbon monoxide in the presence of a hydroformylation catalyst to give an aldehyde, or a mixture of aldehydes, having one more carbon atom than the starting olefin. Thus ethylene yields propionaldehyde, whilst propylene yield a mixture of n- and isobutyraldehydes, of which the straight chain n-isomer is usually the more commercially desirable material. In some cases the catalyst can be modified so that the products are not aldehydes but are the corresponding alcohols.

The catalysts first used in this reaction were cobalt-containing catalysts, such as cobalt octacarbonyl. The use of such catalysts necessitates exceptionally high operating pressures, e.g. several hundred bars, in order to maintain the catalysts in their active form. The n-/iso-molar ratio of the aldehyde products is not particularly high, e.g. about 3:1 or 4:1, and product recovery is generally complicated because the cobalt carbonyl catalysts are volatile and chemically unstable in the absence of high hydrogen and carbon monoxide partial pressures.

Modified forms of cobalt carbonyls have also been described in the literature as hydroformylation catalysts. For example, British Patent Specification No. 988941 proposes the use as hydroformylation catalyst of a cobalt complex containing at least one biphyllic ligand containing trivalent phosphorus, the three valencies of the phosphorus atom being satisfied with any organic group and the organic group optionally satisfying two of the phosphorus valencies to form a heterocyclic compound. Such complexes yield, however, alcohols rather than aldehydes as the major hydroformylation product.

More recently there have been proposed rhodium complex hydroformylation catalysts for hydroformylation of alpha-olefins, that is to say compounds containing the group $-CH=CH_2$ or $>C=CH_2$. These catalysts generally comprise rhodium in complex combination with carbon monoxide and with a ligand, such as triphenylphosphine and are used in conjunction with excess ligand. Such rhodium complex catalysts are now in use in numerous hydroformylation plants throughout the world and many plants formerly operating with cobalt catalysts have been, or are being, converted for operation with these newer rhodium catalysts. Such catalysts have the advantage not only of lower operating pressures e.g. about 20 kg/cm² absolute (19.6 bar) or less, but also of being capable of yielding high n-/iso-aldehyde product ratios from alpha-olefins; in many cases n-/iso-aldehyde molar ratios of 10:1 and higher can be achieved, Moreover, since the catalyst is non-volatile, product recovery is greatly simplified. A fuller description of the process will be found in the article "Low-pressure OXO process yields a better product mix", Chemical Engineering, Dec. 5, 1977. Also extremely relevant to this process are United States Patent Specification No. 3,527,809 and British Patent Specifications Nos. 1,338,237 and 1,582,010.

The rhodium catalyst adopted in commercial practice comprises rhodium in complex combination with carbon monoxide and with triphenylphosphine. Although the nature of the catalytic species is not entirely clear, it has been postulated to be $HRh(CO)(PPh_3)_3$ (see, for example, page 792 of "Advanced Inorganic Chemistry" (Third Edition) by F. Albert Cotton and Geoffrey Wilkinson, published by Interscience Publishers). The reaction solution contains excess triphenylphosphine and operating temperatures in the range of from about 90° C. to about 120° C. are recommended.

U.S. Pat. No. 3,527,809 also proposes the use of various other ligands, including phosphites, such as triphenylphosphite, in place of triphenylphosphine. Although the use of triphenylphosphite has the advantage that lower operating temperatures can be used, we have found that the catalyst tends to deactivate moderately rapidly, a phenomenon that is accompanied by disappearance of free triphenylphosphite ligand and by an increase in the rate of formation of "heavy" materials (i.e. high boiling byproducts). The rate of deactivation when using triphenylphosphite is much greater than when using triphenylphosphine as ligand.

Deactivation of the catalyst and loss of triorganophosphorus ligand (e.g. triphenylphosphine) due to chemical combination with various other components of the reaction system has been noted previously in the literature. For example U.S. Pat. No. 4,151,209 teaches a method of reducing losses of the triorganophosphine ligand by stripping the liquid reaction medium to a degree such that the concentration of all high-boiling organophosphorus reaction by-products, defined as being those organophosphorus by-products which are less volatile than the triorganophosphorus ligand being employed in the process, excluding the oxide of the ligand or a phosphorus containing added inert solvent, is maintained at a level not exceeding that at which the ratio of the phosphorus contained in said high boiling organophosphorus compounds to the phosphorus contained in the ligand which is present does not exceed about 0.2. To compensate for lost catalytic activity Example I proposes increasing rhodium concentration in order to maintain catalyst activity. Both gas stripping, which necessitates high gas recycle rates, and distillation, a procedure requiring the use of vacuum distillation, are proposed when using triphenylphosphine as ligand.

There are numerous other references in the literature to the use of phosphite ligands in homogeneous rhodium complex hydroformylation catalysts. Examples include U.S. Pat. Nos. 3,499,933, 3,547,964, 3,560,539, 3,641,076, 3,644,446, 3,859,359, 3,907,847, 3,917,661, 3,933,919, 3,956,177, 4,096,192, 4,101,588, 4,107,079, 4,108,905, 4,135,911, 4,158,020, 4,195,042, 4,200,591, 4,200,592, 4,224,255, 4,262,142 and 4,267,383, as well as British Patent Specifications Nos. 995,459, 1,207,561, 1,228,201, 1,243,189, 1,243,190, 1,263,720, 1,325,199, 1,338,225, 1,448,090, 1,455,645, 1,460,870, 1,461,900, 1,462,342, 1,463,947, 1,557,396, 1,586,805, 2000124A and 2068377A, European Patent Publications Nos. 0003753 and 0028892, and International Patent Publication No. WO 80/00081.

Other examples include Japanese Patent Publications Nos. 10765/69 published 19th May 1969 and 40326/73 published Nov. 30th 1973.

There is a need to develop a process for the production on a continuous basis of aldehydes, from internal olefins as well as alpha-olefins, which enables operation at relatively low temperatures and pressures.

The present invention accordingly seeks to provide a continuous process for the production of a wide variety of aldehydes from olefins containing alpha-olefinic and/or internal olefinic carbon-carbon bonds which takes advantage of the relatively low operating pressure and temperatures afforded by use of rhodium complex hydroformylation catalysts.

According to the present invention there is provided a continuous hydroformylation process for the production of an aldehyde by hydroformylation of an olefin which comprises:

providing a hydroformylation zone containing a charge of a liquid reaction medium having dissolved therein a complex rhodium hydroformylation catalyst comprising rhodium in complex combination with carbon monoxide and with a phosphite ligand of the general formula:

(RO)$_3$P    (I)

in which each R represents an optionally substituted hydrocarbyl radical;

supplying said olefin to the hydroformylation zone;

maintaining temperature and pressure conditions in the hydroformylation zone conducive to hydroformylation of the olefin;

supplying make-up hydrogen and carbon monoxide to the hydroformylation zone;

recovering from the liquid hydroformylation medium a hydroformylation product comprising at least one non-linear aldehyde; and supplying make-up phosphite ligand to the hydroformylation zone at a rate sufficient to maintain a predetermined level of free phosphite ligand in the hydroformylation medium.

The catalyst used in the process of the present invention is a rhodium carbonyl complex comprising rhodium in complex combination with carbon monoxide and with a cyclic organic phosphite ligand of the general formula (I). Preferably this catalyst and the reaction medium are substantially halogen-free. Although the structure of such rhodium carbonyl complexes is not entirely clear, it is postulated that the preferred halogen-free complexes may have the structure:

RhH$_m$(CO)$_n$[(RO)$_3$P]$_p$ in which m is zero, 1 or 2, and n and p are each, independently of the other, an integer of from 1 to about 4, provided that the sum of m, n and p is from 4 to 6.

The olefin contains at least one olefinic carbon-carbon double bond (or ethylenic bond). Preferably the olefin contains from 2 to about 20 carbon atoms. Included within the term "olefin" are not only alpha-olefins, i.e. olefins containing the radical —CH:CH$_2$ or >C:CH$_2$ but also internal olefins containing the radical —CH:CH—, —CR$_1$:CH—, or —CR$_1$:CR$_1$— where R$_1$ is an organic radical, as well as compounds containing both alpha-olefinic and terminal olefinic groups.

Illustrative olefins include olefinically unsaturated hydrocarbons, e.g., alkenes, arylalkenes, and cycloalkenes, as well as substituted olefins, e.g. ethers of unsaturated alcohols, and esters of unsaturated alcohols and/or acids.

As examples of olefins there may be mentioned alpha-olefins (e.g. ethylene, propylene, butene-1, iso-butylene, pentene-1, 2-methylbutene-1, hexene-1, heptene-1, octene-1, 2,4,4-trimethylpentene-1, 2-ethylhexene-1, nonene-1, 2-propylhexene-1, decene-1, undecene-1, dodecene-1, octadecene-1, eicosene-1, 3-methylbutene-1, 3-methylpentene-1, 3-ethyl-4-methylpentene-1, 3-ethylhexene-1, 4,4-dimethylnonene-1, 6-propyldecene-1, 1,5-hexadiene, vinyl cyclohexane, allyl cyclohexane, styrene, alpha-methylstyrene, allylbenzene, divinylbenzene, 1,1-diphenylethylene, o-vinyl-p-xylene, p-vinylcumene, m-hexylstyrene, 1-allyl-4-vinylbenzene, beta-vinylnaphthalene, and the like), alpha-alkenols, (e.g. allyl alcohol, hex-1-en-4-ol, oct-1-en-4-ol, and the like), alpha-alkenyl ethers (e.g. vinyl methyl ether, vinyl ethyl ether, allyl ethyl ether, allyl t-butyl ether, allyl phenyl ether, and the like), alpha-alkenyl alkanoates (e.g. vinyl acetate, allyl acetate, and the like), alkyl alpha-alkenoates (e.g. methyl acrylate, ethyl acrylate, n-propyl oct-7-enoate, methyl methacrylate, and the like), alpha-olefinically unsaturated aldehydes and acetals (e.g. acrolein, acrolein dimethyl and diethyl acetals, and the like), alpha-olefinically unsaturated nitriles (e.g. acrylonitrile, and the like), and alpha-olefinically unsaturated ketones (e.g. vinyl ethyl ketone, and the like). The term olefin also includes internal olefins which contain preferably from 4 to about 20 carbon atoms. Such compounds have the general formula:

R$_1$R$_2$C=CR$_3$R$_4$ in which R$_1$ and R$_3$ each represent a hydrogen atom or an organic radical or together represent a divalent radical which, together with the indicated carbon atoms, form a carbocyclic or heterocyclic ring, and R$_2$ and R$_4$ each represent an organic radical or together represent a divalent radical which, together with the indicated carbon atoms, form a carbocyclic or heterocyclic ring.

As examples of internal olefins there may be mentioned cis- and trans-butene-2, 2-methylbutene-2, 2,3-dimethylbutene-2, 1,2-diphenylethylene, hexene-2, hexene-3, cis-and trans-heptane-2, decene-2, tetradecene-2, 4-amyldecene-2, 4-methyltridecene-2, octadecene-2, 6,6-dipropyldecene-3, prop-1-enylbenzene, 3-benzylheptene-3, cyclobutene, cyclopentene, cyclohexene, cycloheptene, cyclooctene, 1-methylcyclohexene, diethyl maleate, diethyl fumarate, crotonaldehyde, crotonaldehyde dimethyl acetal, ethyl cinnamate, cis- and trans-prop-1-enyl t-butyl ether, and the like.

Besides the olefin(s), and hydrogen and carbon monoxide, there may also be supplied to the hydroformylation one or more inert materials, such as inert gases (e.g. nitrogen, argon, carbon dioxide and gaseous hydrocarbons, such as methane, ethane, and propane). Such inert gases may be present in the olefin feedstock or in the synthesis gas. Other inert materials may include hydrogenation byproducts of the hydroformylation reaction, e.g. n-butane where the olefin is butene-1 or butene-2.

In many cases the process may be operated so that a part only of the make-up olefin, e.g. from about 15% to about 80% or higher, is converted in passage through the hydroformylation zone. Although the process can be operated on a "once through" basis, with unreacted olefin being exported beyond battery limits, possibly for other uses, after product recovery, it will usually be desirable to recycle unreacted olefin, after product recovery, to the hydroformylation zone. As some isomerisation of olefin may occur in passage through the hydroformylation zone (e.g. in the case of butene-2 some isomerisation to butene-1 may occur) when using $C_{4+}$ olefins, the recycle olefin stream may in such cases contain a minor amount, typically about 10% or less, if isomerised olefin, even though the olefin feedstock is substantially free from other isomeric olefin(s). In addition it may contain byproduct hydrogenated feedstock. The concentration of isomerised olefin(s) and of inert materials in the recycle stream or streams can be controlled in the usual way by taking purge streams at appropriate controlled rates.

It is also within the scope of the invention to utilise mixed feedstocks containing both internal and alpha-olefin components. For example, it is possible to use a mixed $C_4$ hydrocarbon feedstock containing, in addition to cis- and trans-butene-2, also butene-1, iso-butylene, n-butane, iso-butane, and minor amounts of $C_{1-5}$ alkanes. In this case the alpha-olefins butene-1 and iso-butylene will mainly be converted to the corresponding aldehydes, i.e. mainly n-valeraldehyde and 3-methyl-butyraldehyde respectively, whilst the internal olefins cis- and trans-butene-2 are converted mainly to 2-methylbutyraldehyde.

The organic phosphite ligand has the general formula:

$$(RO)_3P \qquad (I)$$

in which each R is an optionally substituted hydrocarbyl radical; the radicals R may be the same or different from one another. Illustrative radicals R include aryl, alkaryl, aralkyl, alkyl, cycloalkyl, alkoxyaryl, hydroxyaryl, alkoxyalkyl, and hydroxyalkyl radicals. Representative radicals R include phenyl, naphthyl, o-tolyl, 2-ethylphenyl, 2,6-dimethylphenyl, 4-t-butylphenyl, 4-iso-pentylphenyl, nonylphenyl, benzyl, 2-phenylethyl, 4-phenylbutyl, methyl, ethyl, n-propyl, iso-propyl, n-butyl, sec-butyl, t-octyl, n-decyl, iso-decyl, n-dodecyl, cyclohexyl, cyclopentyl, 4-methylcyclohexyl, p-methoxyphenyl, p-hydroxyphenyl, 2-ethoxyethyl, 2-hydroxyethyl, and the like.

The preferred ligand is triphenyl phosphite. Other suitable ligands include methyl diphenyl phosphite, tricyclohexyl phosphite, tri-o-tolyl phosphite, tri-(2-ethylphenyl) phosphite, tri-(2,6-dimethylphenyl) phosphite, di-iso-decyl phenyl phosphite, tri-(nonylphenyl) phosphite and the like.

The rhodium complex catalyst is dissolved in a liquid reaction medium in the process of the invention. This reaction medium comprises, in addition to the catalytic species, product aldehyde(s), aldehyde condensation products, internal olefin, hydrogenation product(s) derived from the internal olefin, and a predetermined level of free phosphite ligand. The nature of the aldehyde condensation products, and possible mechanisms for their formation during the course of the hydroformylation reaction, is explained in more detail in British Patent Specification No. 1,338,237, to which reference should be made for further information. Additionally the reaction medium may comprise an added inert solvent, such as benzene, toluene, acetone, methyl iso-butyl ketone, t-butanol, n-butanol, tetralin, decalin, ethyl benzoate and the like. Usually, however, it will be preferred to operate in a "natural process solvent", i.e. a mixture of olefinically unsaturated compound, hydrogenation product(s) thereof, aldehyde product(s) and aldehyde condensation products. However, when operating continuously, it may be preferred to use at start up an inert solvent, such as acetone, benzene, toluene, or the like, and then gradually to allow this to be displaced by "natural process solvent" by differential evaporation as the reaction progresses.

The rhodium concentration in the liquid reaction medium may vary from about 10 ppm or less up to about 1000 ppm or more, calculated in each case as rhodium metal and on a weight/volume basis. Typically the rhodium concentration in the liquid reaction medium lies in the range of from about 40 ppm up to about 200 ppm, calculated as rhodium metal. For economic reasons it will not usually be desirable to exceed about 500 ppm rhodium, calculated as metal, in the liquid reaction medium.

In the liquid reaction medium the phosphite ligand:Rh molar ratio is greater than about 1:1 and preferably greater than about 2:1. At all events the reaction medium should contain a predetermined level of free phosphite ligand. Typically this level is at least about 0.001% w/v, and preferably at least about 0.01% w/v. Even more preferably the ligand:Rh molar ratio is from about 3:1 or 4:1 up to about 20:1 or more. The upper limit of concentration of phosphite ligand in the reaction medium will usually be about 10% w/v or the solubility limit of the phosphite ligand therein, whichever is the lower figure. Usually, however, it will be preferred to operate at phosphite ligand concentrations of less than about 1% w/v and phosphite ligand:Rh molar ratios of from about 5:1 up to about 16:1, e.g. about 8:1. Good results can often be obtained at concentrations of 0.5% w/v or less, e.g. 0.25% w/v or less, of phosphite ligand.

In practising the process of the invention the make-up phosphite ligand may be added continuously or intermittently. It may be added as the essentially pure compound or as a solution in a suitable solvent, e.g. one of the inert solvents mentioned. If continuous addition is chosen then it can be continuously added in solution form with the aid of a suitable dosing pump.

It is generally found that, when starting up a continuous process according to the invention in an inert solvent, such as acetone, the rate of addition of make-up phosphite ligand required to maintain the predetermined level of free phosphite ligand in the reaction medium varies with time. In particular the required rate of addition of make-up ligand under such circumstances appears to rise to a peak and then fall off with time until it reaches an essentially constant level. Whilst it is not intended that the accuracy of the following hypothesis shall in any way affect the validity of our invention, it is postulated that the reason for this phenomenon is that loss of phosphite ligand is occurring at least in part by way of reaction with aldehyde product to give 1:1, 2:1 and 3:1 aldehyde:phosphite adducts and the like as described by F. Ramirez, Pure & Applied Chemistry (1964), Vol 9, pages 337 to 369, at page 356 et seq. Initially, whilst the aldehyde concentration in the reaction medium is low the rate of loss of phosphite is correspondingly low; as this concentration increases by replacement of inert solvent by "natural process solvent" so the aldehyde concentration, and hence the rate of phosphite loss, reaches a peak. However, as time elapses, so the concentration of "heavies" increases and the aldehyde concentration falls correspondingly, thereby reducing the rate of loss of phosphite. An additional factor is the possibility of the phosphite ligand undergoing ester exchange with hydroxy compounds in the reaction medium, for example with aldehyde condensation products, to form more stable phosphite bodies that are still capable of forming catalytically active complexes with rhodium. Eventually essentially steady state conditions are achieved; this state is typically reached after at least about 300 hours of operation. Of course the required rate of addition of make-up ligand and the time needed to achieve steady state conditions will vary with changes in ligand and with changes in operating conditions, e.g. changes in temperature, in rhodium concentration, and in the other operating variables.

When using triphenylphosphite, for example, we have found that, at a rhodium concentration of about 200 ppm, it suffices to add of the order of about 0.04 gms of triphenylphosphite per hour per liter of reaction medium in order to maintain a level of free phosphite ligand of about 0.001% w/v in the reaction medium when hydroformylating butene-2 at 75° C. during the initial stages of reaction.

The hydroformylation conditions utilised in the process of the present invention involve use of elevated temperatures e.g. in the range of from about 40° C. up to about 160° C. or more. Usually, however, it will be preferred to operate at as low a temperature as is possible, consistent with achieving a satisfactory reaction rate, so as to minimise the risk of isomerisation of the olefin. Hence preferred operating temperatures usually range from about 70° C. up to about 130° C.; such temperatures are usually adequate for terminal olefins containing the group —CH=CH$_2$ or for internal olefins containing the group —CH=CH—. The reaction rate depends inter alia on the ligand:Rh molar ratio. Hence it will usually be necessary to increase the operating temperature, if the ligand:Rh molar ratio is increased beyond about 8:1, in order to maintain a substantially constant aldehyde productivity. When using ligand:Rh ratios of from about 3:1 to about 8:1, temperatures of about 70° C. to about 100° C. are usually suitable for terminal olefins containing the group —CH=CH$_2$ or for internal olefins containing the group —CH=CH—; higher temperatures, e.g. up to about 130° C., may be desirable if higher ligand:Rh molar ratios, e.g. about 12:1 or more, are used. Higher temperatures may, however, be necessary where the olefinic carbon-carbon bond is more hindered, as for example when the olefin contains the group —CR$_1$=CH$_2$, —CH=CR$_1$— or —CR$_1$=CR$_1$—, where R$_1$ is an organic radical (the free valencies indicated in the formulae for these radicals are in each case attached to an organic radical); for example, temperatures up to about 150° C. or higher may be necessary in this case in order to achieve satisfactory reaction rates. Use of such higher operating temperature will usually be accompanied by use of higher ligand:Rh molar ratios, e.g. about 8:1 or higher.

Elevated pressures are also typically used in the hydroformylation zone. Typically the hydroformylation reaction is conducted at a total pressure of from about 4 bar upwards up to about 75 bar or more. Usually it will be preferred to operate at a total pressure of not more than about 35 bar.

In the hydroformylation reaction 1 mole of carbon monoxide and 1 mole of hydrogen react with each olefinic bond. Thus, for example, in the case of butene-2, the principal product is 2-methylbutyraldehyde; which is formed by the reaction:
CH$_3$.CH:CH.CH$_3$+H$_2$+CO=CH$_3$.CH(CHO).CH$_2$.CH$_3$.

A small amount of the isomeric aldehyde, n-valeraldehyde, typically less than 5% of the total aldehydes formed, may also be formed as follows:
CH$_3$.CH:CH.CH$_3$+H$_2$+CO=CH$_3$.CH$_2$.CH$_2$.CH$_2$.CHO.

In addition some of the olefin may undergo hydrogenation; hence n-butane may be a byproduct when butene-2 is hydroformylated. Typically less than 5% of the olefin undergoes hydrogenation.

In the case of butene-1, the principal product is n-valeraldehyde whilst the minor product is iso-valeraldehyde.

3-methylbutyraldehyde is the principal product when iso-butene is hydroformylated by the process of the invention:
(CH$_3$)$_2$C:CH$_2$+H$_2$+CO=(CH$_3$)$_2$CH.CH$_2$.CHO.

In operating the process of the invention in a continuous manner it is desirable to supply make up amounts of hydrogen and carbon monoxide in an approximately 1:1 molar ratio, e.g. about a 1.05:1 molar ratio. The formation of such mixtures of hydrogen and carbon monoxide can be effected by any of the methods known in the art for producing synthesis gas for hydroformylation, e.g. by partial oxidation of a suitable hydrocarbon feedstock such as natural gas, naptha, fuel oil or coal.

In operating the process of the invention the total pressure of hydrogen and carbon monoxide in the hydroformylation zone can range from about 1.5 bar or less up to about 75 bar or more. The partial pressure of hydrogen may exceed that of carbon monoxide, or vice versa. For example the ratio of the partial pressures of hydrogen and of carbon monoxide may range from about 10:1 to about 1:10. At all events it will usually be desirable to operate at a partial pressure of hydrogen of at least about 0.05 bar up to about 30 bar and at a partial pressure of carbon monoxide of at least about 0.05 bar up to about 30 bar.

Product recovery can be effected in any convenient manner. In some instances, for example when using butene-1 or butene-2 as the olefinically unsaturated compound, it is possible to utilise a gas recycle process similar to that described in British Patent Specification No. 1582010. More usually, however, it will be more convenient to withdraw a portion of the liquid reaction medium from the hydroformylation zone either continuously or intermittently and to distil this in one or more stages under normal, reduced or elevated pressure, as appropriate, in a separate distillation zone in order to recover the aldehyde product(s) and other volatile materials in vaporous form, the rhodium-containing liquid residue being recycled to the hydroformylation zone. Condensation of the volatile materials and separation thereof, e.g. by distillation, can be carried out in conventional manner. Aldehyde product(s) can be passed on for further purification, whilst a stream containing unreacted internal olefin can be recycled to the hydroformylation zone together with any hydrogen and carbon monoxide that was dissolved in the reaction medium. A bleed stream can be taken from the recycle stream or streams in order to control build up of inerts (e.g. N$_2$) and of hydrogenation product(s) in the recycle streams.

The rhodium may be introduced into the reaction zone in any convenient manner. For example, the rhodium salt of an organic acid, such as rhodium acetate, i.e. [Rh(OCOCH$_3$)$_2$.H$_2$O]$_2$, can be combined with the ligand in the liquid phase and then treated with a mixture of carbon monoxide and hydrogen, prior to introduction of the olefin. Alternatively the catalyst can be prepared from a carbon monoxide complex of rhodium, such as dirhodium octacarbonyl, by heating with the phosphite ligand which thereby replaces one or more of the carbon monoxide molecules. It is also possible to start with the ligand of choice and finely divided rhodium metal, or with an oxide of rhodium (e.g. $Rh_2O_3$ or $Rh_2O_3.H_2O$) and the ligand, or with a rhodium salt of an inorganic acid, such as rhodium nitrate (i.e. $Rh(NO_3)_3.2H_2O$) and the ligand, and to prepare the active species in situ during the course of the hydroformylation reaction. Yet again it is possible to introduce into the reaction zone, as a catalyst precursor, a rhodium complex such as (pentane-2,4-dionato) dicarbonyl rhodium (I) which is then converted, under the hydroformylation conditions and in the presence of excess ligand, to the operative species. Other suitable catalyst precursors include $Rh_4(CO)_{12}$ and $Rh_6(CO)_{16}$.

When using polymeric aldehyde condensation products as solvent, the ratio of aldehyde to such products in the liquid reaction mixture in the hydroformylation zone may vary within wide limits. Typically this ratio lies in the range of from about 1:5 to about 5:1 by weight.

Under appropriate conditions aldehyde productivities in excess of about 0.5 g. moles/liter/hr can be achieved in the process of the invention. Hence it is usually preferred to supply make up olefin to the hydroformylation zone at a rate which corresponds to the aldehyde productivity of the system under the hydroformylation conditions selected. As the conversion per pass will usually be less than 100%, typically about 15% to about 80% or higher, it will be necessary to increase correspondingly the feed rate of the make up olefin if the process is to operate on a "once through" basis or to recycle unreacted olefin at an appropriate rate if the process operates with olefin recycle. Often the aldehyde productivity rate exceeds about 1.0 g. mole/liter/hr, e.g. up to at least about 1.5 g. moles/liter/hr and the rate of supply of make up olefin must then equal or exceed this value.

In the course of our experiments we have found that, when hydroformylating butene-2 using triphenylphosphine as ligand in a rhodium-catalysed hydroformylation system, it is necessary to raise the reaction temperature to about 120° C. in order to get commercially acceptable rates of hydroformylation. At this temperature, however, significant amounts of butene-2 are isomerised to butene-1, with the result that significant amounts of n-valeraldehyde are produced instead of the desired 2-methylbutyraldehyde. In addition the catalyst loses its activity over a period of time and the reaction solution changes colour from a clear yellow to a muddy brown solution which has little or no catalytic activity. Although the mechanism of deactivation is not entirely clear it is believed that rhodium clusters having phosphido bridges of the type:

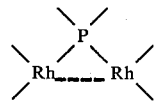

may be formed, this occurring by way of loss of one or more phenyl groups from the triphenylphosphine molecule. (In this formula the free valencies on the rhodium atoms may be attached to at least one other rhodium atom, whilst each of the free valencies on the phosphorus atom is attached either to an organic group, such as phenyl, or to a further rhodium atom). When triphenylphosphine is replaced by triphenylphosphite reaction commences at lower temperatures, e.g. about 70° C., even with butene-2, but catalytic activity also declines fairly rapidly. Analysis of the reaction medium shows that triphenylphosphite is disappearing from the medium at a low rate as the reaction proceeds. If ligand is added to the reaction zone at a rate sufficient to compensate for the observed loss in ligand concentration then substantially constant aldehyde productivity can be maintained for protracted periods of time: the product selectivity is also substantially constant over the same time period.

The invention is illustrated further in the following Examples.

EXAMPLE 1

The continuous hydroformylation of butene-2 was investigated using a stainless steel reactor of nominal capacity 300 ml which is fitted with a magnetically coupled stirrer and with an internal cooling coil through which air could be blown for temperature control purposes. The reactor was also fitted with a gas inlet tube for admission of a $CO/H_2$ mixture to the gas space and an inlet tube for liquid butene-2, each in the form of a dip tube ending near the bottom of the reactor, as well as with a liquid outlet tube in the form of a dip tube whose open lower end was positioned at a level corresponding to the surface level of a volume of 150 ml of liquid in the reactor. Butene-2 was charged to a feed vessel which was pressurised to 4.5 kg/cm$^2$ absolute (446 kPa) with $O_2$-free nitrogen and which was connected to the corresponding inlet tube of the reactor by way of a feed pump and a non-return valve. Carbon monoxide and hydrogen were supplied from individual cylinders thereof through individual pressure controllers and then by way of a two channel mass flow controller through an oxygen guard unit (to ensure that the synthesis gas fed to the reactor was oxygen-free).

Liquid in excess of 150 ml together with unreacted gases exited the reactor through the outlet tube and passed through a cooler to a gas-liquid separator which acted as a knock out pot. The gas from the knock out pot was passed through a letdown valve which let its pressure down to atmospheric pressure and was then supplied to a wet gas meter and vented. The separated reactor solution in the knock out pot was maintained at a specific volume using a level controller which let down excess liquid through a capillary tube to a product evaporator consisting of a Liebig condenser packed with Ballotini glass beads. The majority of the liquid passed through the beads and fell into a receiver which was also fitted with a level controller. When this level controller indicated that the liquid in the receiver exceeded a preselected volume hot oil was pumped through the evaporator. The stripped reactor solution was pumped back from the receiver to the reactor at a constant rate by means of a catalyst recycle pump.

The flashed butene-2 and product passed overhead through a cooler to the product receiver, where the majority of the product was collected. Some of the unreacted butene-2 was dissolved in the product condensate, whilst the remainder passed on through a meter.

The reactor was heated by immersion in a thermostatically controlled oil bath, fine temperature control being exerted automatically by blowing air on demand through the internal cooling coil. The level controllers were set that the total liquid inventory of the catalyst containing solution was 200 ml, i.e. an inventory of 50 ml outside the reactor.

To monitor the course of the reaction the gas flow rates were measured and gas chromatographic analyses were performed by sampling the system as follows:

| Sample stream | Components |
|---|---|
| Inlet synthesis gas | $H_2$, CO |
| Exit gas from knock out pot | $H_2$, CO, aldehydes, butenes, butane |
| Butene off gas | $H_2$, CO, butenes, butane, aldehydes |
| Product | Aldehydes, aldehyde by-products, butenes, butane |
| Reactor solution | Aldehydes, aldehyde by-products, butenes, butane, ligand concentration |

$H_2$ and CO were determined using a 1.85 m×4.76 mm o.d. stainless steel column packed with molecular sieve (5 Å) at 110° C. Butenes and butane were determined using a 1.85 m×4.76 mm o.d. stainless steel column packed with Porasil C at 60° C. Aldehydes and aldehyde byproducts were determined using a 1.85 m×4.76 mm o.d. stainless steel column packed with 10% OV 101 on Chromosorb PAW which was temperature programmed to run at 50° C. for 5 minutes and then to increase in temperature at 10° C./minute to 300° C. Ligand concentration was determined using a phosphorus specific flame photometric detector and a 0.46 m×4.76 mm o.d. stainless steel column packed with 10% OV 101 on Chromosorb PAW run at 220° C.

At start up the empty reactor was purged with nitrogen and then pressurised to 29.2 kg/cm$^2$ absolute (2863 kPa) with the CO/$H_2$ mixture and a flow of the hydrogen/carbon monoxide mixture in excess of the anticipated reaction demand was established through the system using the mass flow controllers. Then acetone was charged to the system via the sample point for the product evaporator bottoms using the catalyst recycle pump. When 100 ml of acetone had been charged the reactor stirrer was switched on and adjusted to run at 1500 r.p.m. Once automatic level control had been achieved addition of acetone was terminated. The feedstock pump was then switched on so as to give a butene-2 feed rate of 60 ml/hr and the system allowed to equilibrate under automatic control.

Next 0.1 g [Rh(OCOCH$_3$)$_2$.H$_2$O]$_2$ (equivalent to 0.418 millimoles of Rh) and 0.6 g (1.93 millimoles) triphenylphosphite were charged to the system via the evaporator bottoms sample point. This corresponds to a ligand:Rh molar ratio of 4.6:1. When the system was homogeneous the reactor temperature was raised to 76° C. Onset of reaction was detected by a decrease in the effluent synthesis gas from the knock out pot, accompanied by more frequent operation of the oil pump to the product evaporator and by the appearance of liquid in the product receiver. As the reaction proceeded the acetone initially charged to the system was replaced within the system by product aldehydes.

The effluent synthesis gas flow rate from the knock out pot was measured to be 28 liters/hr (measured at atmospheric pressure) and its composition was 23% $H_2$, 77% CO. The catalyst solution recycle rate was 270 ml/hr. Triphenylphosphite was charged to the system via the sample point at the rate of 0.025 millimoles/hr. Results were obtained as set out in Table I below.

TABLE I

| Time (hours) | Aldehyde productivity (g.mol/ l.hr.) | Product distribution (%) | | | Butene-2 conversion (%) | Free ligand level (% w/v) |
|---|---|---|---|---|---|---|
| | | 2-MBAL | VAL | C$_4^+$ | | |
| 20 | 0.95 | 94 | 4 | 2 | 22.1 | 0.035 |
| 38 | 1.01 | 95 | 4 | 1 | 23.4 | 0.034 |
| 65 | 0.93 | 95 | 3 | 2 | 21.8 | 0.031 |
| 90 | 0.91 | 94 | 4 | 2 | 21.3 | 0.037 |

Notes:
2-MBAL = 2-methylbutyraldehyde
VAL = n-valeraldehyde
C$_4^+$ = n-butane

COMPARATIVE EXAMPLE

The procedure of the above Example was repeated except that, following the initial charge of 0.1 g [Rh(OCOCH$_3$)$_2$.H$_2$O]$_2$, i.e. 0.418 millimoles Rh, and 0.6 g triphenylphosphite, i.e. 1.93 millimoles, no further addition of triphenylphosphite was made. The reactor temperature was 65° C. and the reactor pressure was 29.2 kg/cm$^2$ absolute (2863 kPa). The effluent synthesis gas flow rate from the knock out pot was 30 liters/hr (measured at atmospheric pressure) and this analysed as 24% $H_2$, 76% CO. The results obtained are listed in Table II. In determining the free triphenylphosphite ligand level the temperature of the gas chromatography column was 280° C. The Notes to Table I apply also to Table II.

TABLE II

| Time (hours) | Aldehyde productivity (g.mol/ l.hr.) | Product distribution (%) | | | Butene-2 conversion (%) | Free ligand level (% w/v) |
|---|---|---|---|---|---|---|
| | | 2-MBAL | VAL | C$_4^+$ | | |
| 18 | 0.88 | 96.5 | 2.5 | 1.0 | 20.4 | 0.032 |
| 34 | 0.74 | 95.9 | 3.1 | 1.0 | 17.2 | 0.018 |
| 50 | 0.65 | 95.0 | 4.0 | 1.0 | 15.1 | 0.009 |

EXAMPLE 2

Using the general procedure of Example 1 the hydroformylation of butene-2 was investigated using diisodecyl phenyl phosphite as ligand. After introduction of the initial charge of ligand, no further make up ligand was added. The reaction conditions were as follows:
Temperature: 84° C.
Rhodium concentration: 200 ppm
Initial ligand concentration: 0.30% w/v
Pressure: 22.15 kg/cm$^2$ absolute (2173.5 kPa)
Catalyst solution recycle rate: 60 ml/hr
Butene-2 feed rate: 68 ml/hr liquid.
The results are summarised in Table III.

TABLE III

| Time (hours) | Temperature (°C.) | Reaction rate (g mol/l/hr) |
|---|---|---|
| 6 | 84.2 | 1.44 |
| 7 | 84.4 | 1.48 |
| 8 | 84.4 | 1.57 |
| 9 | 84.5 | 1.63 |
| 10 | 84.7 | 1.67 |
| 11 | 84.7 | 1.68 |
| 12 | 84.7 | 1.70 |
| 13 | 84.8 | 1.65 |
| 14 | 84.6 | 1.70 |
| 15 | 84.5 | 1.68 |
| 16 | 84.5 | 1.56 |
| 17 | 84.6 | 1.39 |
| 18 | 84.5 | 1.19 |
| 19 | 84.0 | 1.05 |

TABLE III-continued

| Time (hours) | Temperature (°C.) | Reaction rate (g mol/l/hr) |
|---|---|---|
| 23 | 83.4 | 0.97 |
| 24 | 83.5 | 0.90 |
| 25 | 83.1 | 0.80 |
| 26 | 83.0 | 0.71 |

It will be observed that the productivity declined as the reaction progresses, with fairly rapid deactivation occurring after about 15 hours. This decline in productivity can be ascribed to degradation of the ligand. Over the course of the experiment the colour of the reaction medium changed to a very dark brown, a colour change that frequently accompanies catalyst deactivation when using rhodium complex hydroformylation catalysts.

In a further run the onset of catalyst degradation is successfully deferred by controlled addition of di-isodecyl phenyl phosphite at an appropriate rate.

EXAMPLE 3

Tri-(nonylphenyl) phosphite was used in this Example. The general procedure was similar to that described in Example 2. The reaction conditions were:
Temperature: 78° C.
Rhodium concentration: 200 ppm
Initial ligand concentration: 0.5% w/v
Pressure: 22.15 kg/cm² absolute (2173.5 kPa)
Catalyst solution recycle rate: 60 ml/hr
Butene-2 feed rate: 68 ml/hr liquid.
The results observed were as set out in Table IV.

TABLE IV

| Time (hours) | Temperature (°C.) | Reaction rate (g mol/l/hr) |
|---|---|---|
| 4 | 78.0 | 1.56 |
| 5 | 78.0 | 1.56 |
| 6 | 78.1 | 1.51 |
| 8 | 78.2 | 1.57 |
| 9 | 78.1 | 1.56 |
| 11 | 78.9 | 1.53 |
| 12 | 78.8 | 1.48 |
| 14 | 78.5 | 1.51 |
| 16 | 78.6 | 1.52 |
| 18 | 78.8 | 1.49 |
| 19 | 78.6 | 1.49 |
| 22 | 78.3 | 1.48 |
| 24 | 78.4 | 1.44 |
| 26 | 78.5 | 1.43 |
| 28 | 78.0 | 1.41 |
| 30 | 78.2 | 1.33 |
| 32 | 78.1 | 1.27 |
| 34 | 78.0 | 1.22 |
| 36 | 78.1 | 1.11 |
| 38 | 78.1 | 0.97 |
| 40 | 78.0 | 0.81 |

The selectivity to n-butane was less than 0.5%. The corresponding selectivities to n-valeraldehyde and 2-methylbutyraldehyde were 14.5% and 85% respectively.

It will be observed that after about 28 hours the reaction rate began to fall off significantly.

In a further run the reaction rate is maintained substantially constant for an extended period without significant catalyst deactivation becoming apparent by controlled addition of further tri-(nonylphenyl) phosphite.

What is claimed is:

1. In a hydroformylation process for the production of an aldehyde by hydroformylation of an olefin which comprises contacting an olefin with carbon monoxide and hydrogen in a hydroformylation zone containing a charge of a liquid reaction medium having dissolved therein a catalytic amount of a complex rhodium hydroformylation catalyst comprising rhodium in complex combination with carbon monoxide and with an organic phosphite ligand of the general formula:

$$(RO)_3P \qquad (I)$$

in which each R represents a radical selected from hydrocarbyl radicals and substituted hydrocarbyl radicals under temperature and pressure conditions conducive to hydroformylation of the olefin, the improvement comprising:
continuously supplying olefin and make-up hydrogen and carbon monoxide to the hydroformylation zone; and
supplying make-up phosphite ligand of the general formula (I) to the hydroformylation zone at a rate sufficient to maintain a predetermined level of free phosphite ligand in the liquid reaction medium and thereby to maintain the catalytic activity of the complex rhodium hydroformylation catalyst.

2. A process according to claim 1, in which the organic phosphite is an optionally substituted aryl phosphite.

3. A process according to claim 2, in which the organic phosphite is selected from triphenyl phosphite, tri-(o-tolyl) phosphite, tri-(2-ethylphenyl) phosphite, tri-(2,6-dimethylphenyl) phosphite, di-iso-decyl phenyl phosphite, and tri-(nonylphenyl) phosphite.

4. A process according to claim 1, in which the olefin is butene-2 and the hydroformylation product comprises 2-methylbutyraldehyde.

5. A process according to claim 1, in which the hydroformylation zone is maintained at a temperature of from about 40° C. up to about 160° C., at a total pressure of from about 4 bar up to about 35 bar, at a partial pressure of hydrogen and of carbon monoxide each of at least about 0.05 bar, and at a ratio of partial pressures of hydrogen and of carbon monoxide in the range of from about 10:1 to about 1:10.

6. A process according to claim 1, in which the phosphite ligand:Rh molar ratio is at least about 3:1.

7. A process according to claim 1, in which recovery of the hydroformylation product includes withdrawal of reaction medium from the hydroformylation zone and distillation thereof in one or more stages under normal, reduced or elevated pressure.

8. A process according to claim 7, in which the distillation step yields also a stream comprising unreacted olefin which is recycled to the hydroformylation zone.

9. A process according to claim 1, in which the reaction medium comprises aldehyde product and aldehyde condensation products as solvent.

10. A process according to claim 1, in which the olefin is supplied to the hydroformylation zone at a rate corresponding to at least about 0.5 gram moles per liter of reaction medium per hour.

* * * * *